United States Patent [19]
Apffel, Jr. et al.

[11] Patent Number: 5,331,159
[45] Date of Patent: Jul. 19, 1994

[54] COMBINED ELECTROSPRAY/PARTICLE BEAM LIQUID CHROMATOGRAPHY/MASS SPECTROMETER

[75] Inventors: James A. Apffel, Jr., San Jose; Robert G. Nordman, Palo Alto, both of Calif.

[73] Assignee: Hewlett Packard Company, Palo Alto, Calif.

[21] Appl. No.: 7,464

[22] Filed: Jan. 22, 1993

[51] Int. Cl.$^5$ .............................................. H01J 49/04
[52] U.S. Cl. .................................... 250/288; 250/282
[58] Field of Search .................... 250/288, 288 A, 282

[56] References Cited
U.S. PATENT DOCUMENTS
5,015,845  5/1991  Allen et al. ...................... 250/288 A
5,162,650  11/1992  Bier ................................... 250/282

*Primary Examiner*—Jack I. Berman

[57] ABSTRACT

A liquid chromatography-mass spectrometry system that can be configured as either a particle beam or an electrospray interface is provided. The device incorporates structural elements that are common to both interfaces thereby eliminating the need to have two completely separate ES and PB LC/MS systems. The LC/MS device according to the present invention generally comprises a momentum separator, nozzle housing, mass spectrometer, and a vacuum subsystem. A mass spectrometer housing encloses a quadrupole mass analyzer. When used in the ES mode, and ES source module is coupled into the inventive device. Similarly, when used in the PB mode, a PB source module is coupled into the inventive device along with a separate source PB probe. The mass analyzer chamber can accommodate a particle beam source probe for generating ions from analyte particles. In either mode, the modules can consist of commercially available interfaces modified for use with the inventive device.

16 Claims, 4 Drawing Sheets

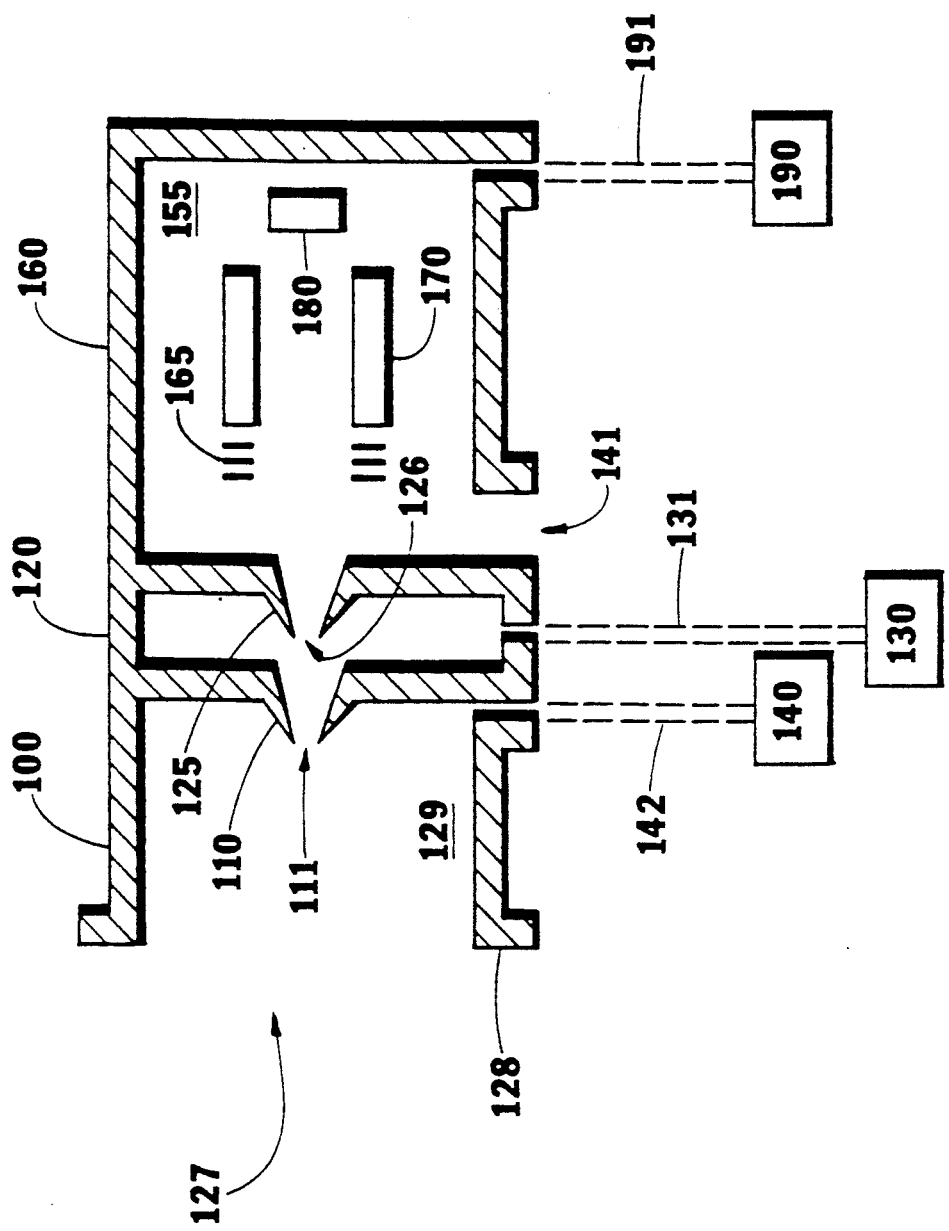
fig. — 1.

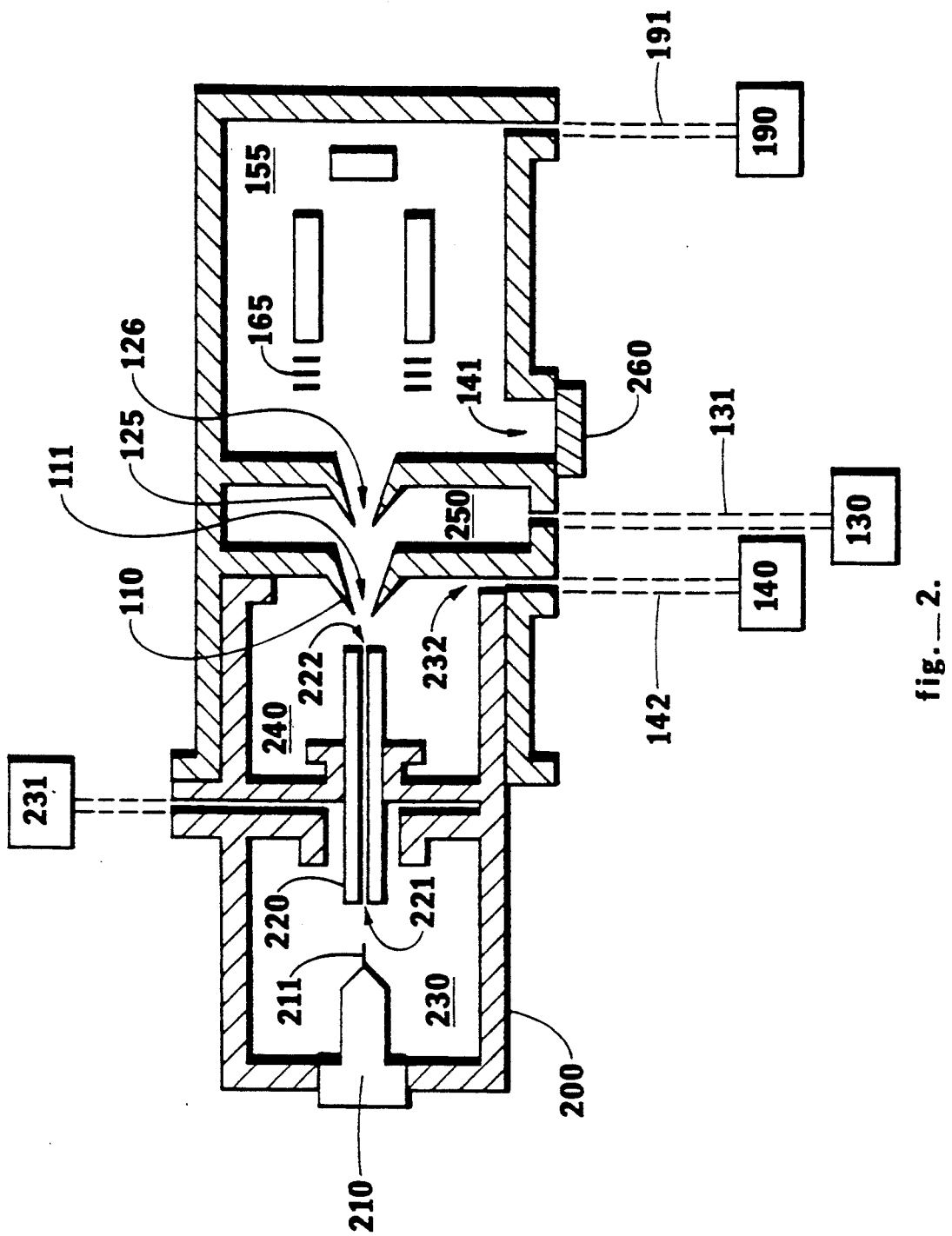
fig.—2.

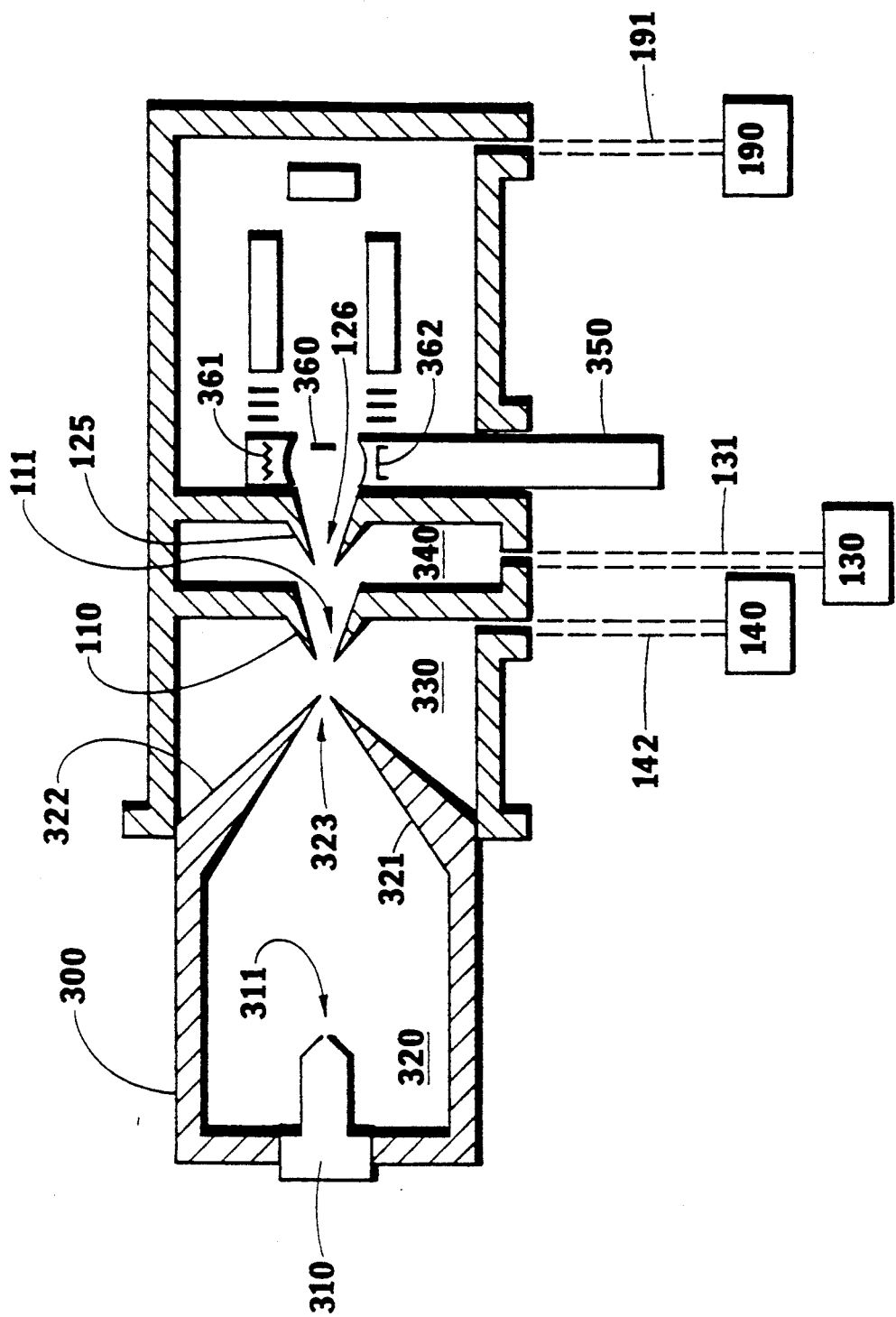

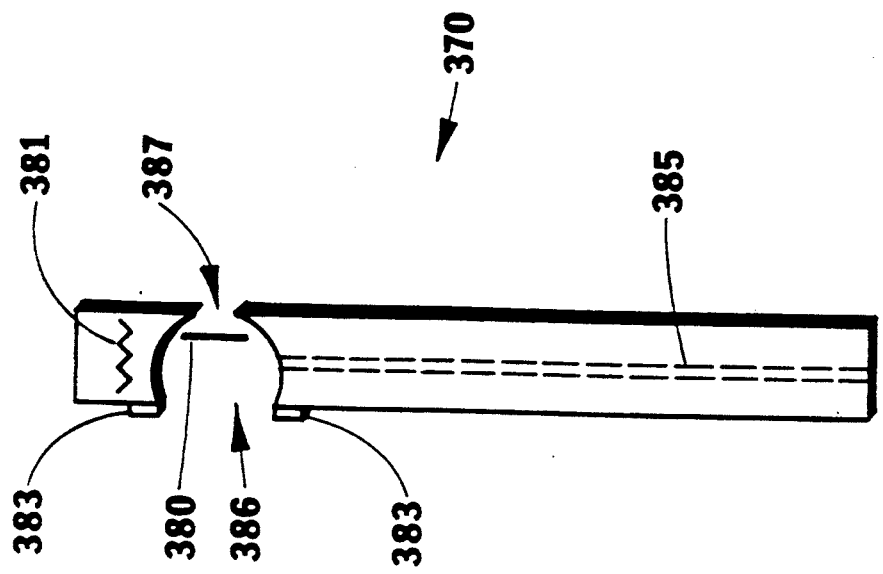
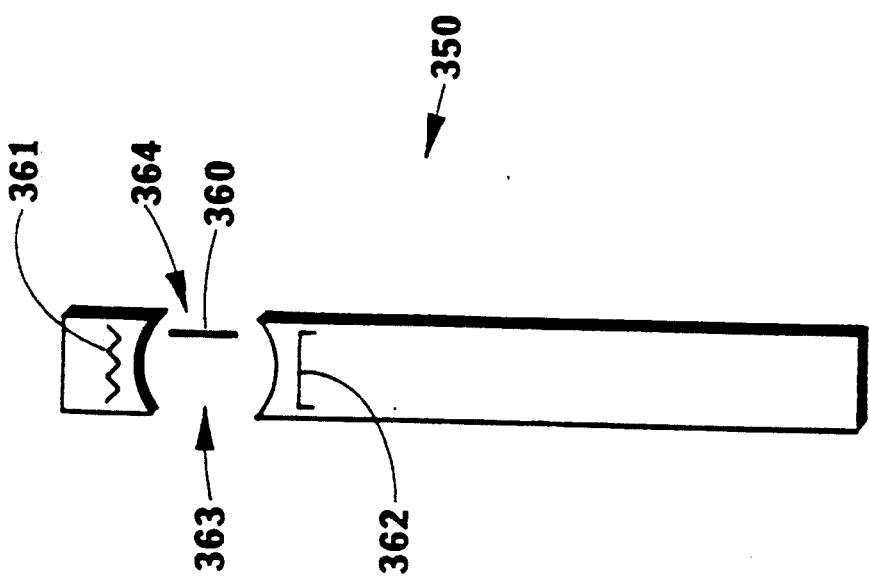

COMBINED ELECTROSPRAY/PARTICLE BEAM LIQUID CHROMATOGRAPHY/MASS SPECTROMETER

FIELD OF THE INVENTION

This invention relates generally to the introduction of samples into a mass spectrometer and more particularly to a mass spectrometer device that can accommodate both electrospray and particle beam interface techniques.

BACKGROUND OF THE INVENTION

Mass spectrometry (MS) has long been a widely accepted analytical technique for obtaining qualitative and quantitative information from a sample. MS is commonly used to determine molecular weight, identify chemical structures, and accurately determine the composition of mixtures. MS is becoming increasingly important in biological research to determine the structure of organic molecules based on the fragmentation pattern of ions formed when sample molecules are ionized.

A well-known analytical technique which combines a separation technique with an analytical detection device is gas chromatography-mass spectrometry (GC-MS). In this method, GC can provide separations of sufficiently volatile compounds which are then ionized and analyzed by mass spectrometry. GC-MS has become established as the definitive analytical technique for amenable compounds, i.e., compounds having sufficient volatility for GC separation and ionization by conventional gas phase electron impact or chemical ionization methods used in mass spectrometry. Such an established capability of broad application is not known to exist for nonvolatile compounds and mixtures.

The coupling of mass spectrometers with liquid chromatography systems has provided a very valuable tool for identifying organic compounds. The unique value of the liquid chromatographic separation systems is their ability to separate solutions containing mixtures of organic compounds into liquid fractions containing individual compounds. However, the product of the liquid chromatographic column is an eluant liquid solution of the compound or compounds to be analyzed that is at atmospheric pressure, whereas the mass spectrometer analyzes compounds in a high vacuum system. Evaporation of the eluant solvent and presentation of the desolvated particles to the mass spectrometer in a suitable form has presented serious difficulties limiting the sensitivity of the mass spectrometer and greatly complicating its efficient operation. Currently Particle Beam (PB) and Electrospray Atmospheric Pressure Ionization (ES-API) Liquid Chromatography/Mass Spectrometers (LC/MS) are the two most popular interface techniques.

In ES-API LC/MS, an electrospray nebulizer produces an aerosol of charged droplets at atmospheric pressure from which desorbed charged analytes are separated. These ions are then electrostatically driven through a multistage separator in which the final pressure is reduced to about $10^{-5}$ torr.

ES-API is a soft ionization technique. For low molecular weight compounds it typically produces singly charged molecular ions and simple spectra. One feature of ES-API is its ability to produce multiple charged ions for high molecular weight compounds; this makes ES-API suitable for analysis of compounds with molecular weights far in excess of the nominal mass range of a quadrupole analyzer. In most designs, by adjusting specific potentials, structurally significant fragmentation can be produced via CID (collision induced dissociation) at the interface. ES-API is best suited for polar compounds, particularly high molecular weight compounds. Current interfaces operate at relatively low flow rates (<100 μl/min), although concentration dependency implies that higher flow rates could be split without loss in sensitivity. Most ES-API designs use a multistage pressure reduction system; some designs employ a large capacity cryopumping mechanism.

In PB LC/MS systems, an aerosol consisting of helium dispersion gas and droplets containing relatively low levels of analyte dissolved in LC effluent is first generated by a nebulizer. The aerosol is injected into a heated desolvation chamber where the volatile components of the droplets (primarily HPLC effluent) are vaporized, resulting in a mixture of helium gas, solvent vapor, and desolvated analyte particles. This mixture then enters a two stage momentum separator in which the less massive components (such as solvent vapor and helium gas) are pumped away while the more massive particles continue through the system and into the mass spectrometer source where the particles are vaporized, ionized, and mass analyzed. The momentum separator also serves as a pressure reduction and sample enrichment device, since most of the gas and solvent are pumped away, while most of the sample enters the mass spectrometer.

Particle Beam LC/MS is capable of producing classical, library searchable electron impact (EI) or chemical ionization (CI) spectra. Since PB relies on gas phase ionization methods, samples must have some degree of volatility. Although this may be significantly less volatility than required for GC/MS analysis, totally nonvolatile samples cannot be analyzed. Furthermore, even those samples that have sufficient volatility may be too thermally labile for EI analysis. In this case, the use of CI can extend the analytical usefulness at the cost of structural information. PB LC/MS is best suited to non-polar compounds with molecular weight less than 1000 amu and low volatility.

SUMMARY OF THE INVENTION

It is an object of the present invention to provide a versatile LC/MS interface system.

It is another object of the present invention to provide a LC/MC device that can accommodate both electrospray and particle beam interfaces.

These and other objects are accomplished with the present invention which is based in part on the discovery that the similarities between electrospray and particle beam interfaces can be exploited in a single system which integrates structural elements common to both. The present invention makes it unnecessary to have two completely separate ES and PB LC/MS systems.

In one aspect of the invention, the inventive combined ES/PB-LC/MS device utilizes structural features that can accommodate either mode of operation, including: momentum separator housing, pump connections, momentum separator pumps, mounting to the mass spectrometer vacuum system, mass spectrometer analyzer, detector, thermostating and vacuum system. Each mode would have a unique "front end." In the case of PB, this includes a nebulizer, desolvation chamber and nozzle. For ES-API, the "front end" includes an electrospray needle, a counterflow nitrogen drying gas, and an entrance capillary.

BRIEF DESCRIPTION OF THE DRAWINGS

FIG. 1 is a cross-sectional view of a schematic of a LC/MS device according to the invention.

FIG. 2 is a cross-sectional view of the device of FIG. 1 coupled to an electrospray interface.

FIG. 3 is a cross-sectional view of the device of FIG. 1 coupled to a particle beam interface.

FIGS. 4A and 4B are cross-sectional views of particle beam source probes.

DESCRIPTION OF PREFERRED EMBODIMENTS

The present invention is based in part on the observation that there are many similarities between electrospray and particle beam interfaces and that a single system which integrates their common structural features significantly increases the efficiency and performance of LC/MS. The inventive system would obviate the need to have two completely separate ES and PB LC/MS systems.

Similarity between the particle beam and electrospray begins with the fact that both systems are based on a method of sample enrichment across a large pressure difference. In the case of PB, a nebulizer produces a sample containing aerosol which is desolvated to produce in a mixture of desolvated sample particles and vapor that is at approximately 200 torr pressure. A two stage momentum separator removes the vapor and reduces the pressure to approximately $10^{-5}$ torr. See Brandt et al., U.S. Pat. No. 4,863,491, issued Sep. 5, 1989, which is incorporated herein. In the case of ES-API, an electrospray nebulizer produces an aerosol of charged droplets at atmospheric pressure that contains charged analytes. These ions are electrostatically driven through a two stage (usually) momentum separator in which the pressure is also reduced to approximately $10^{-5}$ torr. In either method, excess gas and solvent vapor are removed from the system by taking advantage of gas diffusion properties of supersonic jets in momentum separators. PB produces enriched analyte by virtue of the relatively large momentum of the analyte particles (which must be subsequently vaporized and ionized), while ES-API enriches analyte via manipulation of the charged analytes in electric fields.

In terms of instrumentation, the two approaches have very similar requirements. Both systems typically employ quadrupole analyzer systems because (1) unit resolution is usually sufficient; (2) low ion source voltages are used; and (3) there are only moderate vacuum requirements. Other types of analyzers can also be used. The versatility of both systems can be enhanced by using both positive and negative ion modes, although this is not necessary to practice the invention. PB requires a small, but finite degree of volatility, consequently PB generally requires sample molecules to be at least in the 1000 amu range, while for ES-API, the range is 2000 amu or more. Both systems also require a lensing system to focus ions (wherever they are produced) into the quadrupole. Given similar pressure reduction requirements for either mode, it is believed that a non-differentially pumped high vacuum system with a moderate sized diffusion pump (or turbopump) may be sufficient for both.

The solvents utilized in the two systems are similar, with water being the most prevalent, although it is often difficult to work with aqueous solutions. Generally, organic solvents work well. In the case of ES-API, however, the solvent must be sufficiently polar to support charges, although highly conductive buffered solvents are problematic. In both cases, nonvolatile buffers are difficult (although not strictly excluded in ES-API).

While there are differences between electrospray and particle beam techniques, the present invention accommodates these differences without significantly increasing costs. The major difference between the techniques is the method of ionization. ES-API is an ionization technique in which initially generated charged analyte molecules are manipulated through a momentum separator to affect sample enrichment. Consequently, the individual components of the system are held at different potentials relative to each other. In contrast, the components of a PB LC/MS system are all at ground potential. Moreover, PB is a transport technique that requires an ion source to vaporize and ionize the sample particles. Furthermore, ES-API normally uses electronic control systems not needed by PB.

Another important difference between the two systems is that ions approach the respective quadrupoles from different angles. To simplify ion focusing into the quadrupole in ES-API, the ion source is on the axis of the quadrupole electrodes. With PB, on the other hand, particles typically enter the vacuum system at right angles to the quadrupole electrodes where they strike a target and are vaporized, ionized and driven into the quadrupole with a repeller.

The flow regimes of the two systems in prior art devices are also different. For PB the flow rate entering the nebulizer is between 0.1 and 0.5 ml/min. Since PB is a mass sensitive detector, splitting of LC flows will result in proportionally reduced detection limits. For ES-API the flow rate entering the nebulizer is between 1 and 100 $\mu$l/min.

The inventive combined ES/PB-LC/MS device incorporates various structural elements that are applicable for either mode of operation. These elements include: momentum separator housing, pump connections, momentum separator pumps, mounting to the mass spectrometer vacuum system, mass spectrometer analyzer, detector, thermostating and vacuum system. As will be described in detail, the inventive device is designed to accommodate different "front end" apparatuses that are used in conjunction with the device. In the case of PB, the "front end" includes a nebulizer, desolvation chamber and nozzle. For ES-API, the "front end" includes an electrospray needle, a counterflow nitrogen drying gas, and an entrance capillary.

FIG. 1 is a schematic of an inventive LC/MS device which comprises a momentum separator housing 100, nozzle housing 120, mass analyzer (or spectrometer) housing 160, and a vacuum subsystem which includes pumps 130, 140, and 190. Mounted at one end of momentum separator housing 100 is first nozzle (or skimmer) 110. The momentum separator housing is connected through line 131 to pump 130. The nozzles are arranged in series so that second nozzle (or skimmer) 125 is directly behind nozzle 110 such that orifice 126 is directly behind orifice 111. (In other embodiments, the momentum separator may have more than two nozzles that are arranged in series. For instance, in a three stage momentum separator, there would be a third skimmer positioned directly behind the second skimmer. See Dom et al., U.S. Pat. No. 4,980,057, issued Dec. 25, 1990, which is incorporated herein.) Momentum separator housing 100 has port 127 and attachment member 128. The pressure in chamber 129 of momentum separator housing 100 is regulated by pump 140 which is connected to the chamber via line 142. As is apparent, each skimmer has a conical surface which radially narrows to an apex which defines the nozzle orifice or aperture. In addition, each apex faces the port 127 into which an interface device will be inserted.

Situated in chamber 155 of the mass spectrometer housing is a plurality of focusing plates (or lenses) 165, quadrupole rod electrodes 170, and a detector 180. The chamber is connected via line 191 to pump 190. Port 141 can accommodate either an EI or CI source probe for the PB mode as described below. A magnetic deflection, TOF (time-of-flight), Fourier Transform or other type of mass analyzer can be used in place of the quadrupole mass analyzer.

The LC/MS device of FIG. 1 is adaptable to function as either a PB LC/MS or an ES LC/MS apparatus. In the ES mode, as shown in FIG. 2, an ES source module or interface device 200 is inserted into the LC/MS device through port 127 of the momentum separator housing. In operation, LC analyte solution enters nebulizer 210; thereafter, the solution is electrosprayed from needle 211 into module chamber 230. To produce positive ions, the needle point 211 is maintained at a higher potential relative to the inlet 221 of capillary tube 220 through which droplets, ions, and gases enter. Generally, glass capillary 220 has metalized inlet 221 and exit 222 ends.

Electrospray of the analyte solution produces fine, highly charged droplets. These droplets attempt to follow the electric field lines and migrate towards the capillary inlet 221 through a countercurrent stream of bath gas (e.g., nitrogen). The nitrogen enters chamber 230 through a port from bath gas source 231 and exits through port 232. The droplets rapidly evaporate and the solvent vapor along with any other uncharged material is swept away by the flow of bath gas. Desorbed ions arriving in the vicinity of the capillary inlet are entrained in dry bath gas and transported into a two stage pressure reduction subsystem.

The desorbed ions emerge from exit 222 into the first stage vacuum chamber 240 in a supersonic jet of carrier gas. A portion of the free jet flow passes through orifice 111 of skimmer 110 into the second stage vacuum chamber 250, and, thereafter, through orifice 126 of skimmer 125. Most of the remaining solvent molecules that adhere to the analyte ions of interest are removed in the pressure reduction subsystem.

The ions that emerge through orifice 126 are focused by a set of lenses 165 into the mass analyzing chamber 155, where their mass-to-charge ratios (m/z) are determined. When operating in the ES mode, port 141 is sealed by attachment 260.

One important aspect of the inventive device is that the device, with minor modifications, can be used with existing ES or PB interfaces. Commercial ES interfaces manufactured by Analytica of Branford, Inc. (Branford, Conn.) or by Vestec Corp. (Houston, Tex.), for instance, can be readily modified and use as the ES source module shown in FIG. 2.

When the LC/MS device of FIG. 1 is used in the PB mode, as shown in FIG. 3, a PB source module or interface device 300 is inserted into the LC/MS device. In operation, LC analyte solution enters nebulizer 310 where the liquid solution is broken into droplets. Through an opening 311 in the nebulizer a stream of solvent droplets is projected into cylindrical chamber 320. Here the solvent is evaporated, leaving an aerosol or suspension of particles containing a small proportion of residual solvent. The mixture of solvent vapors, gases and desolvated particles is collected by the tapered collector side 321 of the nozzle plate 322 and, by means of the pressure drop across the nozzle, is projected through the nozzle 323 as a supersonic jet.

The gas and particle mixture passes through a two stage momentum separator, wherein the second chamber has a stronger vacuum than the first one. (A separator with more than two stages can be used.) The term "downstream," as used herein, is defined to mean the direction of material flow from weaker vacuum to stronger vacuum. The particles (or dispersion) travel into and through the first chamber 330 of the momentum separator where more of the solvent vapors and other gases are removed from the mixture. The aperture 111 of first stage skimmer 110 is of sufficient diameter so that gases are deflected by the conical surface of the first skimmer.

Upon exiting the first chamber, the dispersion enters into the second chamber 340 where the gases are further expanded and separated from the particles. The mixture continues to travel through the opening 126 of the second skimmer 125. Most of the remaining gases are deflected by the conical surface of the second skimmer. Thereafter, the molecules of interest enter the source volume of the mass spectrometer. In the source volume, particles are initially vaporized; thereafter, the vaporized particles are ionized by electron impact or chemical means into ions which are then focused into the mass analyzer.

As illustrated in FIG. 3, the elongated EI PB source probe 350 has been inserted into the system through the vacuum lock at port 141 (see FIG. 1) which is at right angles to the quadrupole axis. FIG. 4A is an enlarged view of the probe which comprises heated target or grid 360, filament 361, and collector 362. The analyte particles enter the source volume through entrance 363. The target serves to rapidly vaporize incoming analyte particles into gaseous molecules which are bombarded with a beam of electrons from the heated filament. The electrons are directed toward the collector. The analyte ions exit through aperture 364.

When chemical ionization is employed, the elongated CI PB source probe 370, as shown in FIG. 4B (instead of the EI PB probe) is inserted into the system through the vacuum lock at port 141. The CI PB probe comprises heated target or grid 380, filament 381, and reagent gas channel 385. Seal 383 is attached to the probe and situated along the perimeter of entrance 386. As is apparent, exit aperture 387 of the CI PB source probe is narrower than the aperture 364 of the EI PB source probe. The target serves to vaporize analyte particles and electrons from the heated filament are employed to strike (and ionize) reagent gases (typically, methane or ammonia) that are introduced through channel 385. The ionized reagent gases in turn ionized the analyte gaseous molecule by proton transfer. The CI PB source probe fits closely to the back face of the second skimmer to cause a tight seal resulting in sufficiently high source pressure for chemical ionization. In the case of particle beam electron impact spectra, this seal would not be present, which results in a third "phantom" stage of momentum separation. In light of the ES-API ionization method, PB CI might be redundant and this sealing system would not be needed. In the embodiment shown above, there is no isolation valve between the interface and high vacuum. To change from PB to ES, therefore, the system would have to vented.

It is to be understood that while the invention has been described above in conjunction with preferred specific embodiments, the description and examples are intended to illustrate and not limit the scope of the invention, which is defined by the scope of the appended claims.

It is claimed:

1. A liquid chromatography-mass spectrometry system adaptable for use with either a particle beam or electrospray interface device, said system comprising:
   momentum separator housing that defines one or more momentum separator chambers, wherein the housing forms a coupling means to a plurality of different types of interface devices;
   momentum separator that includes one or more nozzles and one or more pumps
   mass analyzer housing that defines a mass analyzer chamber wherein the mass analyzer housing is attached to said momentum separator housing;
   means for analyzing the mass of ions, said mass analyzing means being positioned in said means analyzer chamber; and
   means for focusing ions into said mass analysis means.

2. The liquid chromatography-mass spectrometry system as defined in claim 1 wherein said momentum separator comprises two or more nozzles wherein each of said nozzles has an aperture and wherein said nozzles are arranged in series.

3. The liquid chromatography-mass spectrometry system as defined in claim 2 wherein said nozzles are positioned to receive a mixture of gaseous solvent molecules and analyte molecules or ions that is emitted from said interface device and wherein said nozzles are adapted to separate and remove some of said gaseous solvent molecules.

4. The liquid chromatography-mass spectrometry system as defined in claim 3 wherein each of said nozzles has a conical surface which radially narrows to an apex opposed to said interface device, and wherein said apex defines an aperture.

5. The liquid chromatography-mass spectrometry system as defined in claim 4 wherein said mass analyzer chamber defines a port wherein the port forms a coupling means to a particle beam source probe.

6. The liquid chromatography-mass spectrometry system as defined in claim 5 wherein said particle beam source probe comprises means for ionizing the analyte molecules.

7. The liquid chromatography-mass spectrometry system as defined in claim 1 wherein said interface device is a particle beam source module that defines an evaporation chamber, wherein said particle beam source module comprises:
   nebulizer means for receiving a liquid solution containing analyte and solvent molecules and for projecting a stream of said analyte and solvent molecules into said evaporation chamber, wherein said evaporation chamber is adapted to vaporize said solvent molecules and to project a jet of solvent vapors, gases, and desolvated analyte molecules towards a nozzle of said momentum separator.

8. The liquid chromatography-mass spectrometry system as defined in claim 7 further including a particle beam source probe that is inserted into the port of the mass analyzer chamber, wherein the particle beam source probe comprises means for ionizing the analyte molecules.

9. The liquid chromatography-mass spectrometry system as defined in claim 8 wherein said momentum separator comprises two or more nozzles wherein each of said nozzles has an aperture and wherein said nozzles are arranged in series.

10. The liquid chromatography-mass spectrometry system as defined in claim 9 wherein said nozzles are positioned to receive a mixture of gaseous solvent molecules and analyte molecules or ions that is emitted from said interface device and wherein said nozzles are adapted to separate and remove some of said gaseous solvent molecules.

11. The liquid chromatography-mass spectrometry system as defined in claim 10 wherein each of said nozzles has a conical surface which radially narrows to an apex opposed to said interface device, and wherein said apex defines an aperture.

12. The liquid chromatography-mass spectrometry system as defined in claim 1 wherein said interface device is an electrospray source module that defines a module chamber, wherein said electrospray source module comprises:
   nebulizer means for receiving a liquid solution containing analyte and solvent molecules and for electrospraying, from a needle that is attached to said nebulizer, said liquid solution to form charged droplets containing analyte ions and solvent molecules into said module chamber;
   a source of bath gas that is in communication with said module chamber, said bath gas source adapted to provide bath gas as a carrier for some of said solvent molecules; and
   a capillary tube having an inlet that receives said analyte ions from said module chamber and an outlet from which said analyte ions exit.

13. The liquid chromatography-mass spectrometry system as defined in claim 12 wherein said momentum separator comprises two or more nozzles wherein each of said nozzles has an aperture and wherein said nozzles are arranged in series.

14. The liquid chromatography-mass spectrometry system as defined in claim 13 wherein said nozzles are positioned to receive a mixture of gaseous solvent molecules and analyte molecules or ions that is emitted from said interface device and wherein said nozzles are adapted to separate and remove some of said gaseous solvent molecules.

15. The liquid chromatography-mass spectrometry system as defined in claim 14 wherein each of said nozzles has a conical surface which radially narrows to an apex opposed to said interface device, and wherein said apex defines an aperture.

16. The liquid chromatography-mass spectrometry system as defined in claim 15 wherein said mass analysis means comprises a quadrupole mass analyzer and wherein said focusing means comprises a plurality of lenses.

* * * * *

UNITED STATES PATENT AND TRADEMARK OFFICE
CERTIFICATE OF CORRECTION

PATENT NO. : 5,331,159
DATED : July 19, 1994
INVENTOR(S) : James A. Apffel, Jr. and Robert G. Nordman It is certified that error appears in the above-indentified patent and that said Letters Patent is hereby corrected as shown below:

Column 4, line 41, "Connections" should read -- connections --;

Column 4, line 67, "Dom" should read -- Dorn --;

Column 7, line 24, "means" (second occurrence) should read --mass--.

Signed and Sealed this

Twenty-eight Day of February, 1995

Attest:

BRUCE LEHMAN

Attesting Officer     Commissioner of Patents and Trademarks